United States Patent [19]

Sanders

[11] 4,407,961

[45] Oct. 4, 1983

[54] ION-EXCHANGE SYSTEM AND METHOD FOR ISOLATION AND DETERMINATION OF GLYCOSYLATED HEMOGLOBIN IN HUMAN BLOOD

[76] Inventor: James L. Sanders, 841 N. Zang Blvd., Apt. #236, Dallas, Tex. 75208

[21] Appl. No.: 244,265

[22] Filed: Mar. 16, 1981

[51] Int. Cl.$^3$ .............................................. G01N 33/72
[52] U.S. Cl. .................................. 436/67; 106/197 C; 210/692; 210/927; 252/184; 260/112 B; 436/178; 521/28
[58] Field of Search ..................... 23/230 B, 901, 913; 252/408, 426, 184; 260/112 B; 106/197 C; 210/692, 927; 521/28; 436/67, 178

[56] References Cited

U.S. PATENT DOCUMENTS

| | | | |
|---|---|---|---|
| 4,166,104 | 8/1979 | Wagner et al. | 23/230 B X |
| 4,169,950 | 10/1979 | Ferguson | 544/158 |
| 4,238,196 | 12/1980 | Acuff et al. | 23/230 B |
| 4,243,534 | 1/1981 | Bulbenko | 23/230 B X |
| 4,268,270 | 5/1981 | Gabbay et al. | 23/913 X |
| 4,269,605 | 5/1981 | Dean et al. | 23/913 X |

FOREIGN PATENT DOCUMENTS 55-101052   8/1980   Japan ..................................... 23/913

OTHER PUBLICATIONS

Sankar, Analytical Chemistry, vol. 50, No. 13, Nov. 1978, pp. 1922-1924.

*Primary Examiner*—Arnold Turk
*Attorney, Agent, or Firm*—Charles D. Gunter, Jr.

[57] ABSTRACT

An ion-exchange system and method is provided for isolating glycosylated hemoglobin (Hb A1) from other hemoglobins in human blood together with a quantitative determination of glycosylated hemoglobin. Separation of the glycosylated hemoglobin is accomplished by the ion-exchange system with little temperature dependence in the range of from about 15°–37° C. and without rigid control of pH and ionic strength. The ion-exchange system lowers the pH of the human blood to about pH=6.9 through the use of a zwitterionic buffer. The ion-exchange system also contains a cation-exchange resin. The preferred composition of the ion-exchange system contains about 0.05 molar 3-(N-morpholino)propanesulfonic acid as the buffer and carboxymethyl dextran as the ion-exchange resin present in an amount of from about 30 milliequivalents to about 50 milliequivalents of binding capacity per liter thereof. According to the method provided, a lysed preparation of human blood is added to the ion-exchange system and mixed, causing the non-glycosylated hemoglobin to bind to the ion-exchange resin and leaving the glycosylated hemoglobin free in solution. The solution containing glycosylated hemoglobin is separated from the ion-exchange resin by filtration. The fractional amount of glycosylated hemoglobin present in the human blood is determined by comparing the absorbance of the glycosylated hemoglobin fraction with the absorbance of a diluted sample of the lysed human blood. The use of a reference material prepared from human blood and containing a known amount of glycosylated hemoglobin facilitates the determination of the unknown concentrations in human blood.

3 Claims, No Drawings

ION-EXCHANGE SYSTEM AND METHOD FOR ISOLATION AND DETERMINATION OF GLYCOSYLATED HEMOGLOBIN IN HUMAN BLOOD

BACKGROUND OF THE INVENTION

This invention relates to the selective separation of glycosylated hemoglobin (Hb Al) from non-glycosylated hemoglobin in human blood. Another aspect of this invention relates to the selective separation of non-glycosylated hemoglobin from human blood using an ion-exchange system which does not require rigid control of pH and ionic strength and which shows little temperature dependence in the range of from about 15°–37° C. Still another aspect of this invention relates to a method for separating glycosylated hemoglobin from non-glycosylated hemoglobin and quantitatively determining the fractional amount of glycosylated hemoglobin present in human blood through use of a reference material prepared from human blood.

Throughout this circulatory life of the human red cell, glycosylated hemoglobin is formed continuously by the adduction of glucose to the N-terminal of the hemoglobin beta chain. This process, which is non-enzymatic, reflects the average exposure of hemoglobin to glucose over an extended period. Several classical studies have shown that glycosylated hemoglobin in diabetic subjects can be elevated 2-3 fold over the levels found in normal individuals. [Trivelli, L. A., et al., 1971, *New Eng. J. Med.* 284: 353; Gonen, B., and Rubenstein, A. H., 1978, *Diabetologia* 15: 1; and Gabbay, K. H., et al., 1977, *J. Clin. Endocrinol. Metab.* 44: 859]. These cited investigators have recommanded that glycosylated hemoglobin serve as an indicator of diabetic control since the glycosylated hemoglobin levels approach normal values for diabetics responding to treatment. Historically, fastening plasma glucose and urinary glucose tests have been employed as measures of diabetic control. The use of glycosylated hemoglobin determinations offers several advantages over these methods: (1) the glycosylated hemoglobin level is unaffected by the ingestion of a recent meal; (2) it appears quite stable in the blood; and (3) it reflects the average blood glucose level over an extended period (3–4 weeks) rather than at a single time point, thus providing a better criterion of diabetic control. Thus, an accurate, reproducible and dependable in vitro quantitative test for glycosylated hemoglobin is important in medicine for the clinical management of diabetic patients.

Glycosylated hemoglobin has been defined operationally as the fast fraction hemoglobins (Hb, Ala, Alb, Alc) which elute first during column chromatography with cation-exchange resin. The non-glycosylated hemoglobin, which consists of the bulk of the hemoglobin, remains attached to the resin and can be removed by lowering the pH or raising the ionic strength of the eluting buffer. In the past, a carboxy derivative of cellulose or polystryene has been commonly employed as the ion-exchange resin. Elution of the glycosylated hemoglobin was accomplished by use of a phosphate buffer containing cyanide. These methods are disclosed in Trivelli, L. A., et al., 1971, *New Eng. J. Med.* 284: 353; and Gabbay, K. H., et al., 1977, *J. Clin. Endocrinol. Metab.* 44: 859. Other methods used to separate glycosylated hemoglobin include high-performance cation-exchange chromatography and electrophoresis. These latter procedures require expensive equipment and usually prove too slow and cumbersome for practical uses.

Difficulties can occur in practicing these methods for separating glycosylated hemoglobin from non-glycosylated hemoglobin. For proper quantitative determinations, the composition, pH and ionic strength of the eluting buffer must be maintained within narrow limits. More importantly, temperature control is critical, usually being confined to a range of 21°–24° C. Such rigid limitations on a procedure can cause operating difficulties beyond the capabilities of many clinical laboratories. Furthermore, substantial amounts of cyanide are used in the eluting buffer and represent a hazard to the user. These problems are described by Simon, M., and Eissler, J., 1980, *Diabetes* 29: 467; Rand, P. G., and Nelson, C., 1980, *Clin. Chem.* 26: 1209; and Schellekens, A. P. M., et al., 1981, *Clin. Chem.* 27: 94.

Thus, a need exists for an ion-exchange system and method for determining glycosylated hemoglobin in human blood which offers ease of handling, has little temperature dependence, does not require rigid control of pH and ionic strength, and uses a minimal amount of cyanide.

SUMMARY OF THE INVENTION

According to the invention, an ion-exchange system and method for separating glycosylated hemoglobin from non-glycosylated hemoglobin and a method for quantitative determination of the glycosylated hemoglobin is provided. The ion-exchange system for selectively binding non-glycosylated hemoglobin in human blood contains a cation-exchange resin and a zwitterionic buffer having a pH of from about 6.4 to 7.2 and a concentration of from about 0.02 molar to about 0.1 molar. Preferably, the ion-exchange system contains about 0.05 molar 3-(N-morpholino)propanesulfonic acid and carboxymethyl dextran as the ion-exchange resin present in an amount of from about 30 milliequivalents to about 50 milliequivalents of binding capacity per liter thereof. According to the invention, a lysed preparation of human blood is added to the ion-exchange system and mixed, causing the non-glycosylated hemoglobin to bind to the ion-exchange resin. The glycosylated hemoglobin remains free in solution. The preferred pH of the ion-exchange system is about pH=6.9. The ion-exchange system lowers the pH of the blood to about pH=6.9 and causes the binding of non-glycosylated hemoglobin without binding glycosylated hemoglobin. The solution containing glycosylated hemoglobin is separated from the resin containing non-glycosylated hemoglobin by filtration. The fractional amount of glycosylated hemoglobin present in human blood is determined by comparing the absorbance of the glycosylated hemoglobin fraction at a particular wavelength with the absorbance of a diluted sample of the lysed human blood. The use of a reference material prepared from human blood and containing a known amount of glycosylated hemoglobin facilitates determination of the unknown concentrations in human blood.

The ion-exchange system and method is dependable, accurate and reproducible. Furthermore, rigid control of pH and ionic strength is not required, and there is little temperature dependence in the range of from about 15°–37° C.

DETAILED DESCRIPTION OF THE INVENTION

The ion-exchange system of the subject invention contains a cation-exchange resin and a zwitterionic buffer having a pH of from about 6.4–7.2 and a concentration of from about 0.02–0.1 molar.

The preferred buffer of the subject invention is 3-(N-morpholino)propanesulfonic acid (MOPS) at a concentration of about 0.05 molar. MOPS is a zwitterionic buffer having a pKa of about 7.20 at 20° C. and a useful buffering range from about pH 6.4 to 7.9. Although the preferred buffer is MOPS, the ion-exchange system of the subject invention works effectively with several zwitterionic buffers having a pKa in the range of from about 6.6–7.5 at 20° C. and having a concentration of from about 0.02–0.1 molar. These buffers include N-2-acetamidoiminodiacetic acid; N-2-acetamido-2-aminoethanesulfonic acid; piperazine-N,N'-bis-2-ethanesulfonic acid; N,N -bis-(2-hydroxyethyl)-2-aminoethanesulfonic acid; and 2-[tris-(hydroxymethyl)methyl] aminoethanesulfonic acid. For separation of glycosylated hemoglobin from non-glycosylated hemoglobin, the preferred system pH should be about pH=6.9. The buffer is used to lower the blood pH to about pH=6.9. Use of a zwitterionic buffer offers several advantages over conventional ionic buffers because buffer interaction with proteins is small, ionic strength is easily controlled, and pH shifts with temperature changes are minimized.

The preferred cation-exchange resin of the subject invention is carboxymethyl dextran with a binding capacity of from about 4.0–5.0 milliequivalents per gram of resin. The dextran is cross-linked and beaded to form a particle of from about 40–120 microns in diameter. For purposes of the method, the preferred amount of the resin in the ion-exchange system is about 40 milliequivalents of binding capacity per liter thereof. Although the preferred cation-exchange resin is carboxymethyl dextran, the ion-exchange system of the subject invention works effectively with several other cation-exchange resins having similar binding properties, including sulfopropyl dextran, carboxymethyl cellulose, carboxy cellulose, carboxymethyl agarose and carboxy polystryene.

The combination of zwitterionic buffer and cation-exchange resin allows a rapid and effective separation of glycosylated hemoglobin from non-glycosylated hemoglobin. Because of the use of the zwitterionic buffer, the ion-exchange system of the subject invention does not require rigid control of pH and ionic strength and has little dependence on temperature in the range of from about 15°–37° C.

Preservatives can be employed to assist in stabilizing the ion-exchange system at room temperature. The preferred preservative is boric acid present in a concentration of about 0.01 molar. Boric acid acts to inhibit microbial growth.

The preferred method of the present invention for the determination of glycosylated hemoglobin includes the following steps and the total test time requires about 15 minutes. About 0.1 millimeters of well-mixed, whole blood is added to about 0.5 milliliters of a lysing agent comprised of about 0.25% polyoxyethylene octyl phenol in water. The polyoxyethylene octyl phenol is a surfactant which acts to disrupt the cell membrane and causes the release of hemoglobin, thus forming a lysate. The preferred molecular weight of the polyoxyethylene octyl phenol is about 650 daltons. Although other volumes can be used, the ratio of lysing agent to whole blood should be approximately constant at 5. Potassium cyanide should also be included in the lysing agent if the whole blood contains significant amounts of methemoglobin. Glycosylated methemoglobin has ion-exchange binding properties which differ from those of the usual glycosylated oxyhemoglobin. The glycosylated methemoglobin binds to the ion-exchange resin causing a falsely low result for the glycosylated hemoglobin determination. Cyanide complexes with methemoglobin to form cyanmethemoglobin. Glycosylated cyanmethemoglobin has ion-exchange properties essentially the same as the binding properties of glycosylated oxyhemoglobin. The inclusion of cyanide in the lysing agent then converts glycosylated methemoglobin to glycosylated cyanmethemoglobin and the correct result is obtained for the glycosylated hemoglobin determination. The preferred concentration of potassium cyanide in the lysing agent is about 0.01 molar.

For separation of glycosylated hemoglobin from non-glycosylated hemoglobin, about 0.1 milliliters of the lysate is added to about 3.0 milliliters of the ion-exchange system and the combined system is mixed for about 5 minutes. Upon addition to the ion-exchange system, the lysate pH is lowered to about pH=6.9. At about pH=6.9, an electrostatic charge difference exists between glycosylated hemoglobin and non-glycosylated hemoglobin, which allows the cation-exchange resin to bind non-glycosylated hemoglobin while leaving glycosylated hemoglobin free in solution. The use of MOPS as the buffer in the preferred method allows pH control at different temperatures. Use of the preferred ion-exchange system assures a fast and effective separation of glycosylated hemoglobin from non-glycosylated hemoglobin in the temperature range of from about 15°–37° C. The resin is separated from the surrounding solution by filtration. More preferably, the ion-exchange system is filtered with a porous-plastic serum filter capable of retaining the resin. (Such filters are available from Glasrock Products, Inc., Fairburn, Georgia). The filtered solution contains glycosylated hemoglobin while the ion-exchange resin retains the non-glycosylated hemoglobin.

The method described herein is preferred for assaying the amount of glycosylated hemoglobin, although any established method for determining hemoglobin may be used. Hemoglobin, both glycosylated and non-glycosylated, absorbs quite strongly in the Soret Band wavelength region of from about 400 nm to about 440 nm. For purposes of the method, absorbance measurements for hemoglobin are made at the preferred wavelength of 415 nm.

The preferred means for expressing the analytical results for glycosylated hemoglobin is as the percent of total hemoglobin—i.e., glycosylated plus non-glycosylated. The absorbance at 415 nm for the glycosylated hemoglobin is made directly on the filtered solution containing glycosylated hemoglobin. The absorbance at 415 nm for total hemoglobin is made on a diluted sample of the blood lysate, prepared by adding about 0.02 milliliters of the blood lysate to about 5.0 milliliters of deionized water and mixing well. The glycosylated hemoglobin as percent of total hemoglobin is then determined by calculating the ratio of absorbances at 415 nm for the glycosylated hemoglobin to the total hemoglobin and comparing the ratio to that of a reference material which is also carried through the separation procedure. The reference material is a stable preparation of human blood and contains a known amount of glycosylated hemoglobin. (Such reference material is available from Sandare Chemical Company, DeSoto, Tex.). The following equation is used:

$$\frac{\text{Ratio (unknown)}}{\text{Ratio (reference)}} \times \frac{\% \text{ Gly Hb in}}{\text{reference}} = \frac{\% \text{ Gly Hb in}}{\text{unknown}}$$

The use of a reference material in the method adjusts for any inaccuracies in volume dispensing and compensates for whatever temperature dependence that might be present.

The method of the subject invention shows linearity in the range of 5% to 20% glycosylated hemoglobin. Bloods having a total hemoglobin concentration exceeding 180 grams per liter should be diluted two-folds with deionized water before assay. Sensitivity of the method indicates a change of about 0.02% glycosylated hemoglobin for every change of 0.001 absorbance units. The final separation fractions appear quite stable, but absorbance measurements should be made within 1 hour of separation before evaporation of the samples becomes significant.

EXAMPLE 1

The ion-exchange system and method of the invention was used to determine the expected values for glycosylated hemoglobin in a non-diabetic population. One hundred subjects were used in the study. These individuals had normal blood glucose values and no history of diabetes. The ion-exchange system contained about 0.05 molar 3-(M-morpholino)propanesulfonic acid and carboxymethyl dextran present in an amount of about 40 milliequivalents of binding capacity per liter thereof. The ion-exchanger system also contained boric acid as a preservative present in an amount of about 0.01 molar. About 0.1 milliliters of well-mixed, whole blood was added to about 0.5 milliliters of a lysing agent comprised of about 0.25% (v/v) polyoxyethylene octyl phenol in water to prepare a lysate. The lysing agent also contained about 0.01 molar potassium cyanide to convert any methemoglobin to cyanmethemoglobin. About 0.1 milliliters of the lysate was added to about 3.0 milliliters of the ion-exchange system and the system was mixed for about 5 minutes. The ion-exchange resin was then separated from the surrounding solution by filtering through a porous-plastic serum filter. A spectrophotometer calibrated to read absorbance at 415 nm was zeroed using deionized water as the blank, and the absorbance of the filtered solution was then determined. The absorbance of the total hemoglobin fraction was made by diluting about 0.02 milliliters of the lysate with about 5.0 milliliters of deionized water and measuring the diluted sample against water as the blank. The glycosylated hemoglobin concentration, expressed as percent of total hemoglobin, was determined by calculating the ratio of the glycosylated hemoglobin absorbance to the total hemoglobin absorbance and comparing the ratio to that of a reference material containing a known amount of glycosylated hemoglobin and carried through the separation. The glycosylated hemoglobin values of the normal subjects ranged from 6.4% to 8.7%.

EXAMPLE 2

The preferred ion-exchange system and method were used to establish the expected values range for a diabetic population. The bloods of 42 individuals diagnosed as diabetic and who were receiving medication for this condition were analyzed using the ion-exchange system and method set forth in Example 1. The glycosylated hemoglobin values for the diabetic subjects ranged from 7.5% to 14.8%, with a mean value of 10.7%. Five of the 42 diabetic subjects had glycosylated hemoglobin values which were within the observed normal range—i.e., 8.7% or below. These five individuals had blood glucose levels close to normal, indicating well-managed treatment. The correlation coefficient was 0.71 between fasting glucose levels and the glycosylated hemoglobin values. Thus, the clear separation of glycosylated hemoglobin expected values for the diabetic and non-diabetic populations, and the general agreement between fasting glucose levels and glycosylated hemoglobin values in the diabetic population, indicate the usefulness and the efficiency of the invention.

EXAMPLE 3

Within run reproducibility of the preferred ion-exchange system and method was determined by conducting separation of glycosylated hemoglobin twenty times each for normal and diabetic bloods using the ion-exchange system and method set forth in Example 1. The following results were obtained:

| TYPE | MEAN | STD DEV | % CV |
| --- | --- | --- | --- |
| NORMAL | 7.8 | 0.21 | 2.7 |
| DIABETIC | 13.4 | 0.23 | 1.7 |

EXAMPLE 4

Run to run reproducibility of the preferred ion-exchange system and method was determined by conducting separation of glycosylated hemoglobin for ten successive runs for both normal and diabetic bloods using the ion-exchange system and method set forth in Example 1. The following results were obtained:

| TYPE | MEAN | STD DEV | % CV |
| --- | --- | --- | --- |
| NORMAL | 7.6 | 0.31 | 4.1 |
| DIABETIC | 13.0 | 0.60 | 4.6 |

EXAMPLE 5

Temperature dependence of the preferred ion-exchange system and method was determined by conducting separation of glycosylated hemoglobin from normal and diabetic bloods at temperatures of 15°, 24°, 30° and 37° C. using the ion-exchange system and method set forth in Example 1. The results showed an average difference of 0.4% glycosylated hemoglobin for separations carried out over the temperature range of 15°–37° C., thus establishing the little temperature dependence of the ion-exchange system.

This invention has been described in detail with reference to its preferred embodiments, and many modifications will now be apparent to those skilled in the art and those modifications are intended to be within the scope of the appended claims.

What is claimed is:

1. An ion exchange system for selectively separating glycosylated hemoglobin from non-glycosylated hemoglobin in a sample of lysated human blood, comprising:

a zwitterionic buffer in a concentration in the ion exchange system of from about 0.02 to 0.1 molar, said buffer having a pH of from about 6.4 to 7.2 and a pKa of from about 6.6 to about 7.5 at 20° C., said zwitterionic buffer being selected from the group consisting of 3-(N-morpholino) porpanesulfonic acid, N-2-acetamidoiminodiacetic acid, N-2-acetamido-2-aminoethanesulfonic acid, piperazine-N,N'-bis-2-ethanesulfonic acid, N,N-bis-(2-hydroxyethyl)-2-aminoethanesulfonic acid, and 2-[tris-(hydroxy-methyl)methyl] aminoethanesulfonic acid; and a cation exchange resin present in the ion exchange system in an amount of from about 30 milliequivalents to about 50 milliequivalents of binding capacity per liter of ion exchange system.

2. A method of separating glycosylated hemoglobin from non-glycosylated hemoglobin and determining the amount of glycosylated hemoglobin in human blood without rigid control of pH and ionic strength and with little temperature dependence comprising the steps of:

preparing a lysate of human blood;

introducing an ion exchange system into said lysate, said ion exchange system including a zwitterionic buffer, said zwitterionic buffer being present in said ion exchange system in a concentration of from about 0.02 to 0.1 molar, said buffer having a pH of from about 6.4 to 7.2 and a pKa of from about 6.6 to about 7.5 at 20° C., said zwitterionic buffer being selected from the group consisting of 3-(N-morpholino) propanesulfonic acid, N-2-acetamidoiminodiacetic acid, N-2-acetamido-2-aminoethane-sulfonic acid, piperazine-N,N'-bis-2-ethanesulfonic acid, N,N-bis-(2-hydroxyethyl)-2-aminoethanesulfonic acid, and 2-[tris-(hydroxymethyl)methyl] aminoethanesulfonic acid, and a cation exchange resin, said cation exchange resin being present in said ion exchange system in an amount of from about 30 milliequivalents to about 50 milliequivalents of building capacity per liter of ion exchange system;

said cation exchange resin being effective in the presence of said buffer to form a bound fraction of non-glycosylated hemoglobin and an unbound fraction of glycosylated hemoglobin in said lysate; and analyzing said bound and unbound fractions for hemoglobin.

3. The method of claim 2, wherein said step of analyzing said bound and unbound fractions comprise the steps of:

(a) separating said bound fraction from said unbound fraction;

(b) determining the absorbance at 415 nm of said unbound fraction;

(c) preparing a dilution of said lysate of human blood in water and determining the absorbance at 415 nm;

(d) calculating the ratio of the absorbance of said unbound fraction to the absorbance of said diluted lysate;

(e) calculating the ratio of absorbance of the unbound fraction to the absorbance of the diluted lysate for a reference material prepared from human blood and containing a known amount of glycosylated hemoglobin;

(f) calculating the glycosylated hemoglobin concentration in said blood by dividing the ratio of absorbances of said blood lysate by the ratio of absorbances of said reference material and multiplying by the glycosylated hemoglobin concentration of the reference material.

* * * * *